United States Patent
Kawakami et al.

(10) Patent No.: US 9,612,218 B2
(45) Date of Patent: Apr. 4, 2017

(54) METHOD FOR DETERMINING WHETHER ACIDIC AQUEOUS SOLUTION IS USABLE

(71) Applicant: MITSUBISHI HEAVY INDUSTRIES, LTD., Tokyo (JP)

(72) Inventors: Tetsuji Kawakami, Tokyo (JP); Hiroyuki Mitsui, Tokyo (JP); Yoshiyuki Inoue, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 71 days.

(21) Appl. No.: 14/761,022

(22) PCT Filed: Feb. 7, 2014

(86) PCT No.: PCT/JP2014/052930
§ 371 (c)(1),
(2) Date: Jul. 15, 2015

(87) PCT Pub. No.: WO2014/129324
PCT Pub. Date: Aug. 28, 2014

(65) Prior Publication Data
US 2015/0355123 A1 Dec. 10, 2015

(30) Foreign Application Priority Data
Feb. 22, 2013 (JP) .................. 2013-033574

(51) Int. Cl.
*G01R 27/08* (2006.01)
*C23G 1/02* (2006.01)
(Continued)

(52) U.S. Cl.
CPC ............ *G01N 27/06* (2013.01); *B08B 3/08* (2013.01); *C23G 1/00* (2013.01); *C23G 1/02* (2013.01); *G01N 27/02* (2013.01); *B08B 13/00* (2013.01)

(58) Field of Classification Search
CPC .......... G01N 27/06; G01N 27/02; C23G 1/00; C23G 1/02; B08B 13/00; B08B 3/08
(Continued)

(56) References Cited

U.S. PATENT DOCUMENTS 6,379,749 B2    4/2002  Zimmerman, Jr. et al.
7,351,391 B1 *  4/2008  Olsen ..................... C01B 7/035
                                              134/3
(Continued)

FOREIGN PATENT DOCUMENTS

EP    2 241 727      10/2010
JP    2003-34887      2/2003
(Continued)

OTHER PUBLICATIONS

International Search Report issued Mar. 4, 2014 in International Application No. PCT/JP2014/052930.
(Continued)

*Primary Examiner* — Amy He
(74) *Attorney, Agent, or Firm* — Wenderoth, Lind & Ponack, L.L.P.

(57) ABSTRACT

This method for determining whether an acidic aqueous solution is usable or not comprises: a first detection step (S21) in which the solution concentration of an acidic aqueous solution resulting from pickling is determined; a second detection step (S23$a$, S23$b$) in which the concentration of a specific metal in the acidic aqueous solution resulting from pickling is determined, the metal having been contained in the coating layer; a concentrated-solution addition step (S25$b$) in which in cases when the solution concentration is equal to or less than a predetermined first threshold, a concentrated acidic aqueous solution is newly added; and a determination step (S24$a$, S24$b$) in which in cases when the concentration of the specific metal is equal to or higher than a predetermined second threshold, it is determined that the acidic aqueous solution is unusable.

6 Claims, 8 Drawing Sheets

(51) Int. Cl.
   *C23G 1/00*   (2006.01)
   *G01N 27/06*  (2006.01)
   *B08B 3/08*   (2006.01)
   *G01N 27/02*  (2006.01)
   *B08B 13/00*  (2006.01)

(58) Field of Classification Search
   USPC .................................................. 324/693, 691
   See application file for complete search history.

(56) References Cited

U.S. PATENT DOCUMENTS

| | | | | |
|---|---|---|---|---|
| 8,876,978 B2 * | 11/2014 | Kawakami | .............. | F01D 5/005 |
| | | | | 134/19 |
| 2002/0130666 A1 * | 9/2002 | Nonaka | .................... | C23G 1/02 |
| | | | | 324/468 |

FOREIGN PATENT DOCUMENTS

| | | |
|---|---|---|
| JP | 2007-182629 | 7/2007 |
| JP | 2009-541582 | 11/2009 |
| JP | 4848460 | 12/2011 |
| JP | 2012-62834 | 3/2012 |
| JP | 2013-217250 | 10/2013 |
| WO | 2009/101690 | 8/2009 |

OTHER PUBLICATIONS

Written Opinion of the International Searching Authority issued Mar. 4, 2014 in International Application No. PCT/JP2014/052930 (with English translation).
Office Action issued May 26, 2015 in corresponding Japanese patent application No. 2013-033574 (with English translation).

\* cited by examiner

… (1)

METHOD FOR DETERMINING WHETHER ACIDIC AQUEOUS SOLUTION IS USABLE

TECHNICAL FIELD

The present invention relates to a method for determining whether an acidic aqueous solution is usable in pickling treatment that peels a coating layer on the surface of a member for gas turbines.

This application claims priority based on Japanese Patent Application No. 2013-033574 filed in Japan on Feb. 22, 2013, of which the contents are incorporated herein by reference.

BACKGROUND ART

The operating temperature of gas turbines has been increasing year by year for the purpose of improving efficiency. To respond to such temperature increases, a coating layer for the purpose of heat shielding (thermal barrier coating: TBC) is formed on the surface of members for gas turbines exposed to high temperatures, for example, gas turbine blades, combustors.

Such coating layers are configured from an undercoating layer formed of an alloy on the base material of a member for gas turbines, and a top coating layer formed of a ceramic on the undercoating layer.

When repairing a member for gas turbines after operation, the coating layer formed on the base material of the member for gas turbines is peeled, and then a coating layer is regenerated by newly forming an undercoating layer and a top coating layer on the base material.

For example, as a method for peeling a coating layer, Patent Document 1 and Patent Document 2 disclose a method in which a member is immersed sequentially in an alkali washing solution, water, and a weak acid washing solution, and then, after heat treatment is performed, immersed in a strong acid washing solution (acidic aqueous solution).

CITATION LIST

Patent Literature

Patent Document 1: WO/2009/101690
Patent Document 2: Japanese Unexamined Patent Application Publication No. 2012-62834A

SUMMARY OF INVENTION

Technical Problem

In the method for peeling a coating layer disclosed in Patent Document 1, the coating layer formed on the surface of a member for gas turbines is removed by peeling via pickling (pickling treatment) in which the member for gas turbines are immersed into the above strong acid washing solution. This strong acid washing solution is reused (repeatedly used). When the strong acid washing solution is repeatedly reused, the dissolved components in the strong acid washing solution due to dissolution of the coating layer increase, and the solution component of the strong acid washing solution decreases, and washing performance is sometimes lost.

When the washing performance of the strong acid washing solution is lost in this manner, there is the possibility of the coating layer formed on the surface of the member for gas turbines remaining partially undissolved and the coating layer remaining.

The present invention provides a method for determining whether an acidic aqueous solution is usable, which enables determination of whether an acidic aqueous solution (strong acid washing solution) that removes a coating layer formed on the surface of a member for gas turbines is usable.

Solution to Problem

According to a first aspect of the present invention, the method for determining whether an acidic aqueous solution is usable is a method for determining whether an acidic aqueous solution is usable in pickling treatment that peels a coating layer on the surface of a member for a gas turbine, the method comprising: a first detection step of detecting a solution concentration of the acidic aqueous solution after the pickling treatment; a second detection step of detecting a concentration of a specific metal in the acidic aqueous solution after the pickling treatment, the metal being contained in the coating layer; a concentrated-solution addition step of newly adding a concentrated acidic aqueous solution when the solution concentration is equal to or less than a predetermined first threshold; and a determination step of determining that the acidic aqueous solution is unusable when the concentration of the specific metal is equal to or higher than a predetermined second threshold.

According to the above method for determining whether an acidic aqueous solution is usable, the method comprises a concentrated-solution addition step of detecting a solution concentration of the acidic aqueous solution after the pickling treatment, and when the solution concentration is equal to or less than a predetermined first threshold, newly adding a concentrated acidic aqueous solution. As a result, the solution concentration of the acidic aqueous solution can be maintained in a state in which the solution concentration exceeds the first threshold. By maintaining the solution concentration of the acidic aqueous solution in a state in which the solution concentration exceeds the first threshold in this manner, the washing capability of the acidic aqueous solution can be held at or above a certain level.

A concentrated acidic aqueous solution is a solution of which the solution concentration (acid concentration) is higher than that of the previously mentioned acidic aqueous solution.

Furthermore, the method comprises a determination step of detecting a concentration of a specific metal in the acidic aqueous solution after the pickling treatment, and determining that the acidic aqueous solution is unusable when the concentration of the specific metal is equal to or greater than a predetermined second threshold. As a result, it can be determined whether the acidic aqueous solution can be further used. When a concentration of a specific metal is detected, it means that the component contained in the coating layer has leached out in the acidic aqueous solution. When the concentration of the specific metal is equal to or greater than the second threshold, the washing capability of the acidic aqueous solution decreases. The concentration of the specific metal is, for example, the concentration of a metal such as Co, Ni, Cr, or Al.

In the above method for determining whether an acidic aqueous solution is usable, the solution concentration of the acidic aqueous solution is maintained in a state in which the solution concentration exceeds the first threshold, and additionally, it can be determined whether the acidic aqueous solution is usable by detecting the concentration of a specific metal. Therefore, it is possible to determine whether the acidic aqueous solution can be further used.

According to a second aspect of the present invention, the method for determining whether an acidic aqueous solution is usable further comprises a liquid volume determination step of determining whether a liquid volume of the acidic aqueous solution exceeds a stipulated volume. In the liquid volume determination step, when the liquid volume is determined to be equal to or less than the stipulated volume, the method comprises: a first detection step of detecting a solution concentration of the acidic aqueous solution after the pickling treatment; a second detection step of detecting a concentration of a specific metal in the acidic aqueous solution after the pickling treatment, the metal being contained in the coating layer; a concentrated-solution addition step of newly adding a concentrated acidic aqueous solution when the solution concentration is equal to or less than a predetermined first threshold; an acidic aqueous solution addition step of newly adding an acidic aqueous solution when the solution concentration exceeds the predetermined first threshold; and a determination step of determining that the acidic aqueous solution is unusable when the concentration of the specific metal is equal to or higher than a predetermined second threshold.

In this case, since it is determined whether the liquid volume of the acidic aqueous solution exceeds a stipulated volume, the liquid volume can be maintained at or above the stipulated volume by adding acidic aqueous solution or adding a concentrated acidic aqueous solution when the liquid volume is less than the stipulated volume. Furthermore, it can be determined whether the acidic aqueous solution is usable by detecting the concentration of a specific metal.

According to a third aspect of the present invention, in the first detection step, electrical conductivity is detected instead of the solution concentration, and in the concentrated-solution addition step, a concentrated acidic aqueous solution is newly added when the electrical conductivity is equal to or less than a predetermined first threshold.

According to a fourth aspect of the present invention, in the first detection step, electrical conductivity is detected instead of the solution concentration, and in the concentrated-solution addition step, a concentrated acidic aqueous solution is newly added when the electrical conductivity is equal to or less than a predetermined first threshold, and in the acidic aqueous solution addition step, an acidic aqueous solution is newly added when the electrical conductivity exceeds the predetermined first threshold.

In this case, since electrical conductivity is detected instead of solution concentration, the first detection step can be performed more easily.

According to a fifth aspect of the present invention, in the second detection step, specific gravity is detected instead of the concentration of a specific metal, and in the determination step, the acidic aqueous solution is determined to be unusable when the specific gravity is equal to or higher than a predetermined second threshold.

In this case, since specific gravity is detected instead of a concentration of a specific metal, the second detection step can be performed more easily. Additionally, when configured such that electrical conductivity is detected in the first detection step and specific gravity is detected in the second detection step, the method for determining whether an acidic aqueous solution is usable can be performed more easily because electrical conductivity and specific gravity can be detected in a shorter time using compact devices.

The acidic aqueous solution may be hydrochloric acid.

In this case, pickling treatment can be performed without degrading members for gas turbines by adding an appropriate corrosion and rust inhibitor.

Advantageous Effects of Invention

According to the above method for determining whether an acidic aqueous solution is usable, it can be determined whether an acidic aqueous solution (strong acid washing solution) that removes a coating layer formed on the surface of a member for gas turbines is usable.

DESCRIPTION OF EMBODIMENTS

First Embodiment

Below, embodiments of the present invention will be described with reference to the appended drawings.

First, the first embodiment will be described with reference to FIGS. 1 to 4.

The method for determining whether an acidic aqueous solution is usable of the present embodiment is a method for determining whether an acidic aqueous solution (strong acid washing solution) used in pickling treatment which peels a coating layer formed on the surface of a member for gas turbines (gas turbine blades, gas turbine vanes, combustors, and the like) is usable.

Examples of the acidic aqueous solution used in pickling treatment include hydrochloric acid, hydrofluoric acid, and the like. This type of acidic aqueous solution is used repeatedly in pickling treatment of the above member for gas turbines. In a repeatedly used acidic aqueous solution, determination is required whether the acidic aqueous solution can be further used because washing power decreases due to decreased solution concentration and increased dissolved components due to dissolution of the coating layer.

In the present embodiment, the acidic aqueous solution is hydrochloric acid. Degradation of members for gas turbines can be prevented by adding an appropriate corrosion and rust inhibitor to hydrochloric acid.

The coating layer formed on the surface of members for gas turbines contains, for example, Co, Ni, Cr, Al, Y, and the like.

Figure 1:
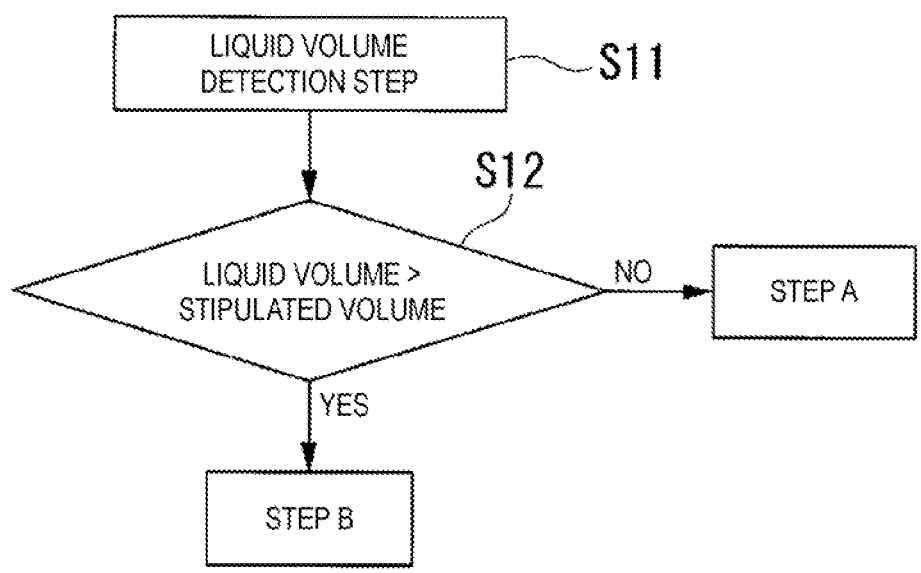
FIG. 1 is a flowchart of a method for determining whether an acidic aqueous solution is usable according to a first embodiment of the present invention.
Figure 2:
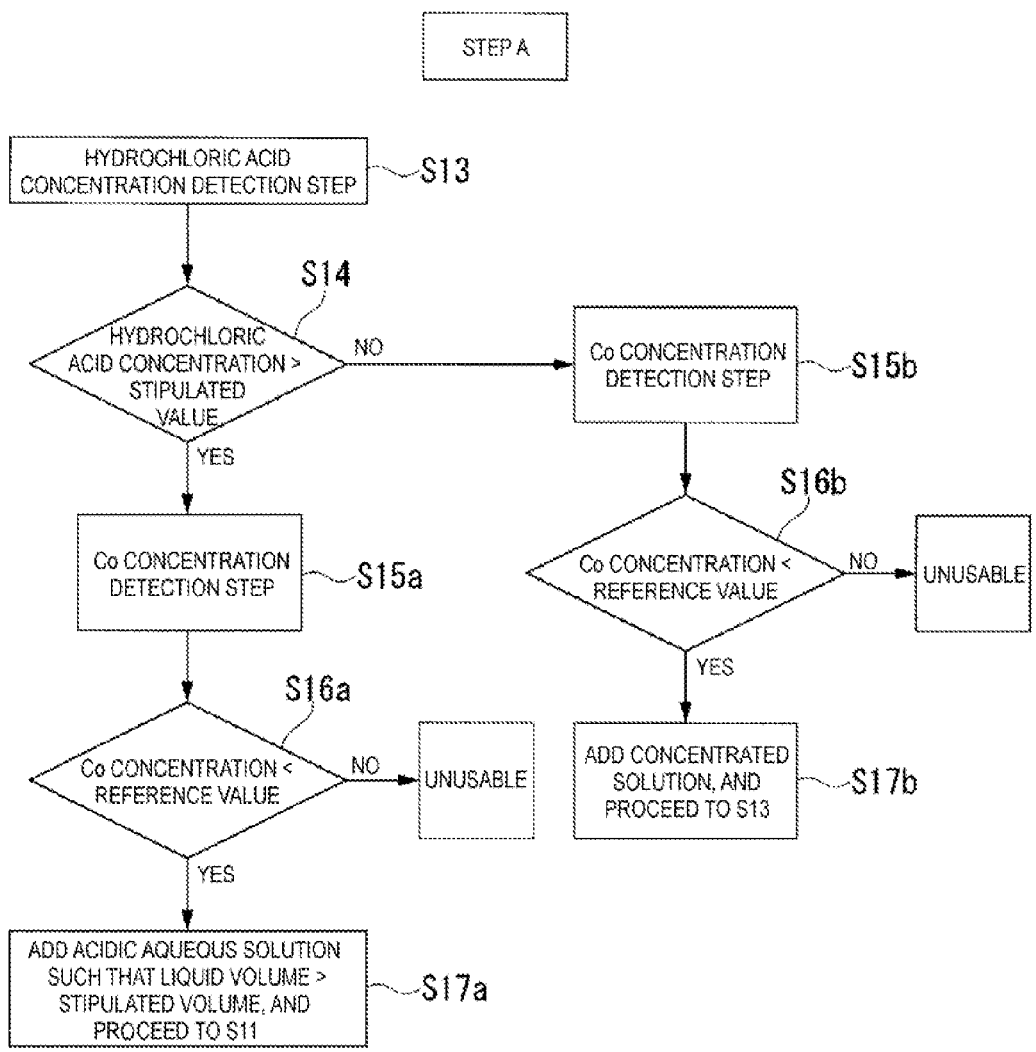
FIG. 2 is a flowchart of step A in FIG. 1.
Figure 3:
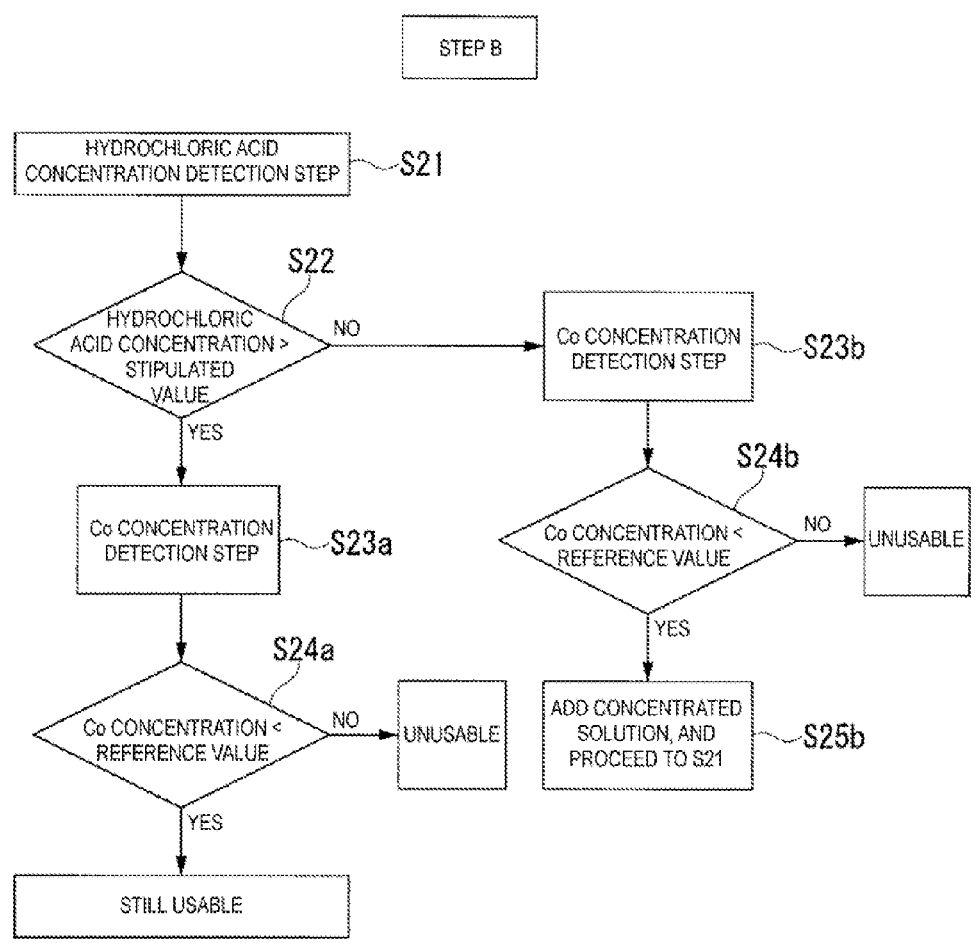
FIG. 3 is a flowchart of step B in FIG. 1.

FIGS. 1 to 3 are flowcharts of the method for determining whether an acidic aqueous solution is usable according to the first embodiment. The method for determining whether an acidic aqueous solution is usable according to the first embodiment comprises, for example, a liquid volume detection step S11, a liquid volume determination step S12, hydrochloric acid concentration detection steps S13 and S21, hydrochloric acid concentration determination steps S14 and S22, Co concentration detection steps S15a, S15b, S23a, and S23b, and determination steps S16a, S16b, S24a, and S24b.

Details of the method for determining whether an acidic aqueous solution is usable according to the first embodiment will be described below.

First, the liquid volume of the acidic aqueous solution (hydrochloric acid) is detected (liquid volume detection step S11). The liquid volume may be measured from, for example, the height of the pickling treatment solution tank.

Then, it is determined whether the liquid volume of the acidic aqueous solution (hydrochloric acid) exceeds a stipulated volume (liquid volume determination step S12). When the liquid volume is equal to or less than the stipulated volume, step A is performed. When the liquid volume exceeds the stipulated volume, step B is performed.

(Step A)

Step A will be described below, using FIG. 2.

In step A, first, hydrochloric acid concentration is detected (hydrochloric acid concentration detection step S13). The hydrochloric acid concentration may be detected by, for example, the neutral titration method in accordance with JIS K8180.

Then, it is determined whether the hydrochloric acid concentration exceeds a stipulated value (first threshold) (hydrochloric acid concentration determination S14). When the hydrochloric acid concentration exceeds the stipulated value, a Co concentration detection step S15a, in which the Co concentration is detected, is performed. When the hydrochloric acid concentration is equal to or less than the stipulated value, a Co concentration detection step S15b, in which the Co concentration is detected, is performed. Co concentration can be detected by, for example, ICP atomic emission spectrometry.

In the Co concentration detection step S15a, when the Co concentration is less than a reference value (second threshold), an acidic aqueous solution (hydrochloric acid) is added such that the liquid volume of the acidic aqueous solution exceeds a stipulated volume (acidic aqueous solution addition step S17a), and the process returns again to the liquid volume detection step S11. In the Co concentration detection step S15a, when the Co concentration is equal to or greater than the reference value, the acidic aqueous solution (hydrochloric acid) is determined to be unusable (determination step S16a). When the acidic aqueous solution is determined to be unusable in this manner, the method for determining whether an acidic aqueous solution is usable according to the present embodiment ends.

In the Co concentration detection step S15b, when the Co concentration is less than the reference value, a concentrated acidic aqueous solution (hydrochloric acid) is added (concentrated-solution addition step S17b), and the process returns again to the hydrochloric acid concentration detection step S13. In the Co concentration detection step S15b, when the Co concentration is equal to or greater than the reference value, the acidic aqueous solution (hydrochloric acid) is determined to be unusable (determination step S16b).

A concentrated solution refers to a solution of which the acid concentration is higher than that of the acidic aqueous solution. In the present embodiment, the concentrated solution refers to a solution with a higher hydrochloric acid concentration than that of the hydrochloric acid used as the acidic aqueous solution.

(Step B)

Step B will be described below, using FIG. 3.

In step B, similar to step A, first, the hydrochloric acid concentration is detected (hydrochloric acid concentration detection step S21).

Then, it is determined whether the hydrochloric acid concentration exceeds a stipulated value (first threshold) (hydrochloric acid concentration determination S22). When the hydrochloric acid concentration exceeds the stipulated value, a Co concentration detection step S23a, in which the Co concentration is detected, is performed. When the hydrochloric acid concentration is equal to or less than the stipulated value, a Co concentration detection step S23b, in which the Co concentration is detected, is performed.

In the Co concentration detection step S23a, when the Co concentration is less than a reference value (second threshold), it is determined that an acidic aqueous solution can be further used. In the Co concentration detection step S23a, when the Co concentration is equal to or greater than the reference value, the acidic aqueous solution is determined to be unusable (determination step S24a).

In the Co concentration detection step S23b, when the Co concentration is less than the reference value, a concentrated acidic aqueous solution is added (concentrated-solution addition step S25b), and the process returns again to the hydrochloric acid concentration detection step S21. In the Co concentration detection step S23b, when the Co concentration is equal to or greater than the reference value, the acidic aqueous solution is determined to be unusable (determination step S24b).

Figure 4:
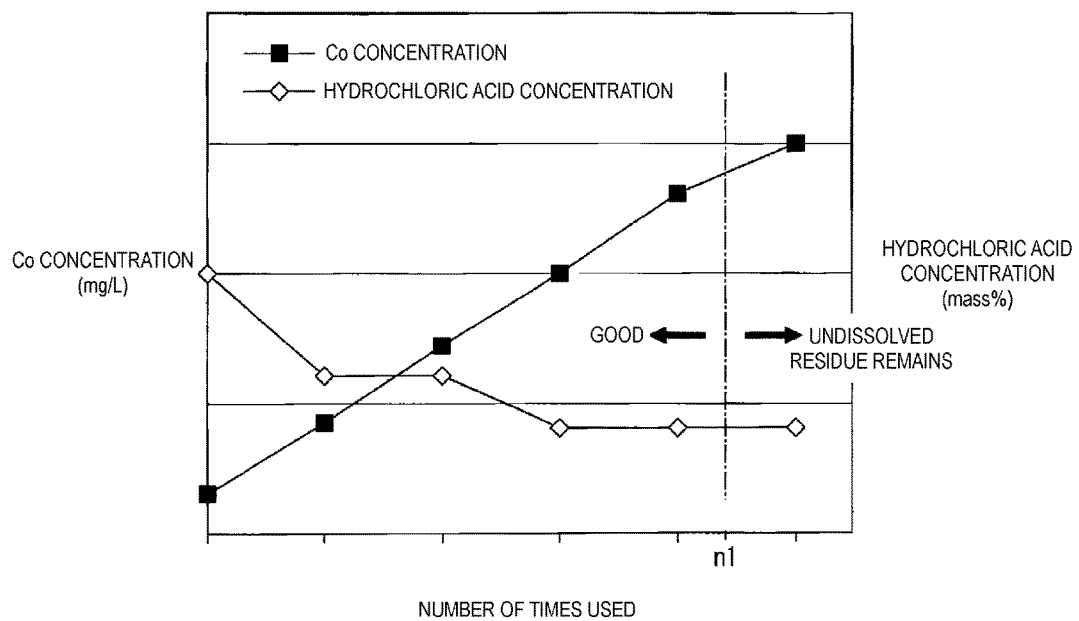
FIG. 4 is a drawing illustrating the relationship between the number of times an acidic aqueous solution is used and Co concentration, and the relationship between the number of times an acidic aqueous solution is used and hydrochloric acid concentration.

FIG. 4 illustrates the relationship between the number of times the acidic aqueous solution is used and the Co concentration detected in the Co concentration detection steps S23a and S23b, and the relationship between the number of times the acidic aqueous solution is used and the hydrochloric acid concentration detected in the hydrochloric acid concentration detection step S21. In FIG. 4, the stipulated value of hydrochloric acid concentration and the reference value of Co concentration are indicated by a single dot-dash line. In FIG. 4, the acidic aqueous solution can be used up to $n_1$ times, which is below the stipulated value of hydrochloric acid concentration and the reference value of Co concentration. The coating layer can be favorably pickled up to $n_1$ times, but if $n_1$ times is exceeded, the coating layer will remain undissolved.

The stipulated value of hydrochloric acid concentration and the reference value of Co concentration can be optionally preset in accordance with the size of the member for gas turbines, the thickness of the coating layer, and the like.

According to the method for determining whether an acidic aqueous solution is usable according to the first embodiment of the present invention described above, the method comprises concentrated-solution addition steps S17b and S25b in which the hydrochloric acid concentration of hydrochloric acid, which is the acidic aqueous solution after pickling treatment, and when the hydrochloric acid concentration is less than a stipulated value, concentrated hydrochloric acid solution is newly added. As a result, the solution concentration (hydrochloric acid concentration) of the acidic aqueous solution (hydrochloric acid) is maintained in a state in which the solution concentration exceeds the stipulated value. By maintaining the solution concentration of the acidic aqueous solution in a state in which the solution concentration exceeds the stipulated value in this manner, the washing capability of the acidic aqueous solution can be held at or above a certain level.

Furthermore, the method comprises determination steps S16a, S16b, S24a, and S24b in which, Co concentration in the acidic aqueous solution after pickling treatment, and when the Co concentration exceeds a reference value, the acidic aqueous solution is determined to be unusable. As a result, it can be determined whether the acidic aqueous solution can be further used. When Co is detected in the acidic aqueous solution, it means that the component contained in the coating layer has leached out in the acidic aqueous solution. When the Co concentration exceeds the reference value, the washing capability of the acidic aqueous solution decreases.

As described above, in the method for determining whether an acidic aqueous solution is usable of the present embodiment, the solution concentration (hydrochloric acid concentration) of the acidic aqueous solution (hydrochloric acid) is maintained at or above a stipulated value, and additionally, it can be determined whether the acidic aqueous solution (hydrochloric acid) is usable by detecting Co concentration. Therefore, it is possible to determine whether the acidic aqueous solution can be further used.

In the present embodiment, the method further comprises a liquid volume determination step S12 in which it is determined whether the liquid volume of the acidic aqueous solution exceeds a stipulated volume. As a result, the liquid volume can be maintained at or above the stipulated volume by adding an acidic aqueous solution when the liquid volume is less than the stipulated volume. Furthermore, after the liquid volume determination step S12, it can also be determined that the acidic aqueous solution is unusable when the Co concentration is determined to be less equal to or more than the reference value.

In the first embodiment, the case where Co concentration is detected has been described, but the concentration of a specific metal such as, for example, Ni, Cr, Al, contained in the coating layer may be detected.

Second Embodiment

Next, a method for determining whether an acidic aqueous solution is usable according to a second embodiment of the present invention will be described.

The second embodiment is configured in the same manner as the first embodiment except that specific gravity is detected instead of Co concentration of the acidic aqueous solution, and electrical conductivity is detected instead of hydrochloric acid concentration of the acidic aqueous solution.

Figure 5:
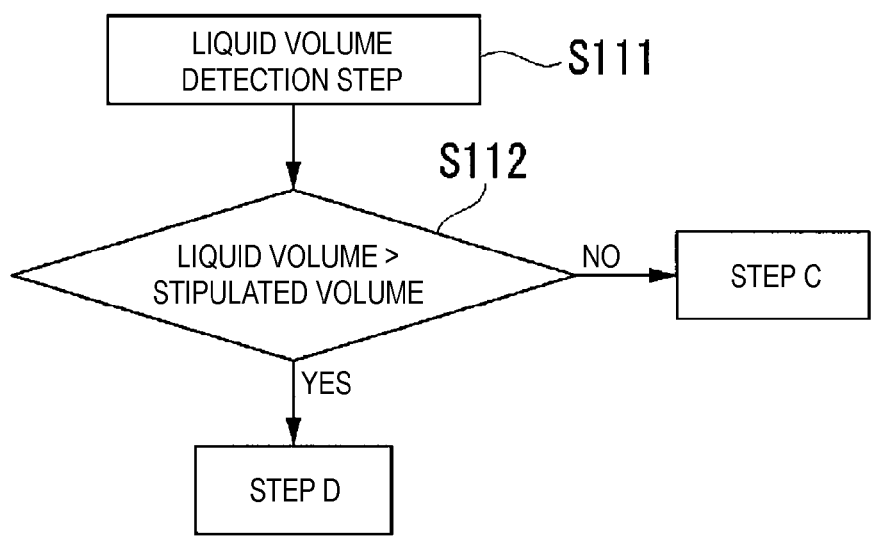
FIG. 5 is a flowchart of a method for determining whether an acidic aqueous solution is usable according to a second embodiment of the present invention.
Figure 6:
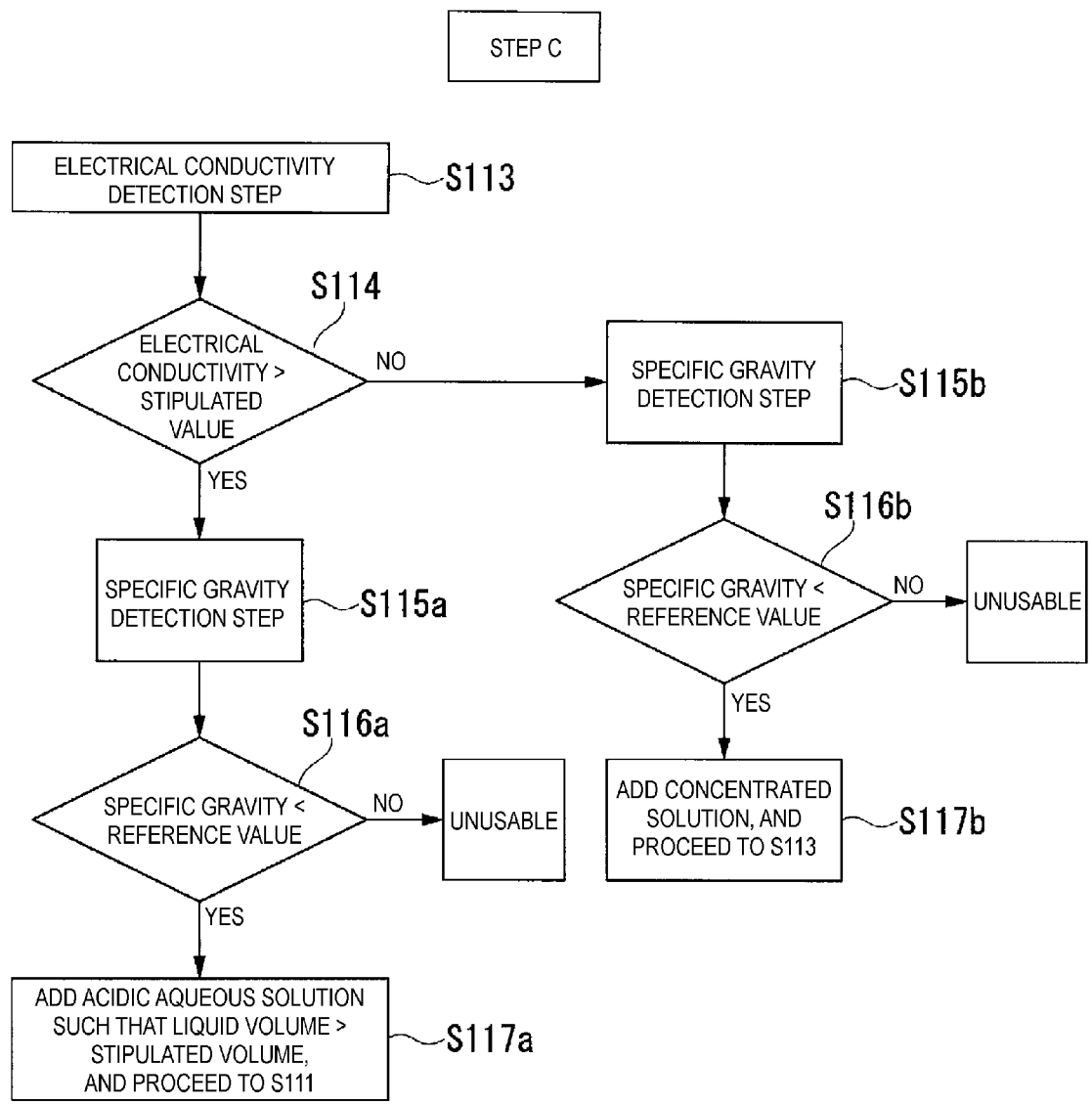
FIG. 6 is a flowchart of step C in FIG. 5.
Figure 7:
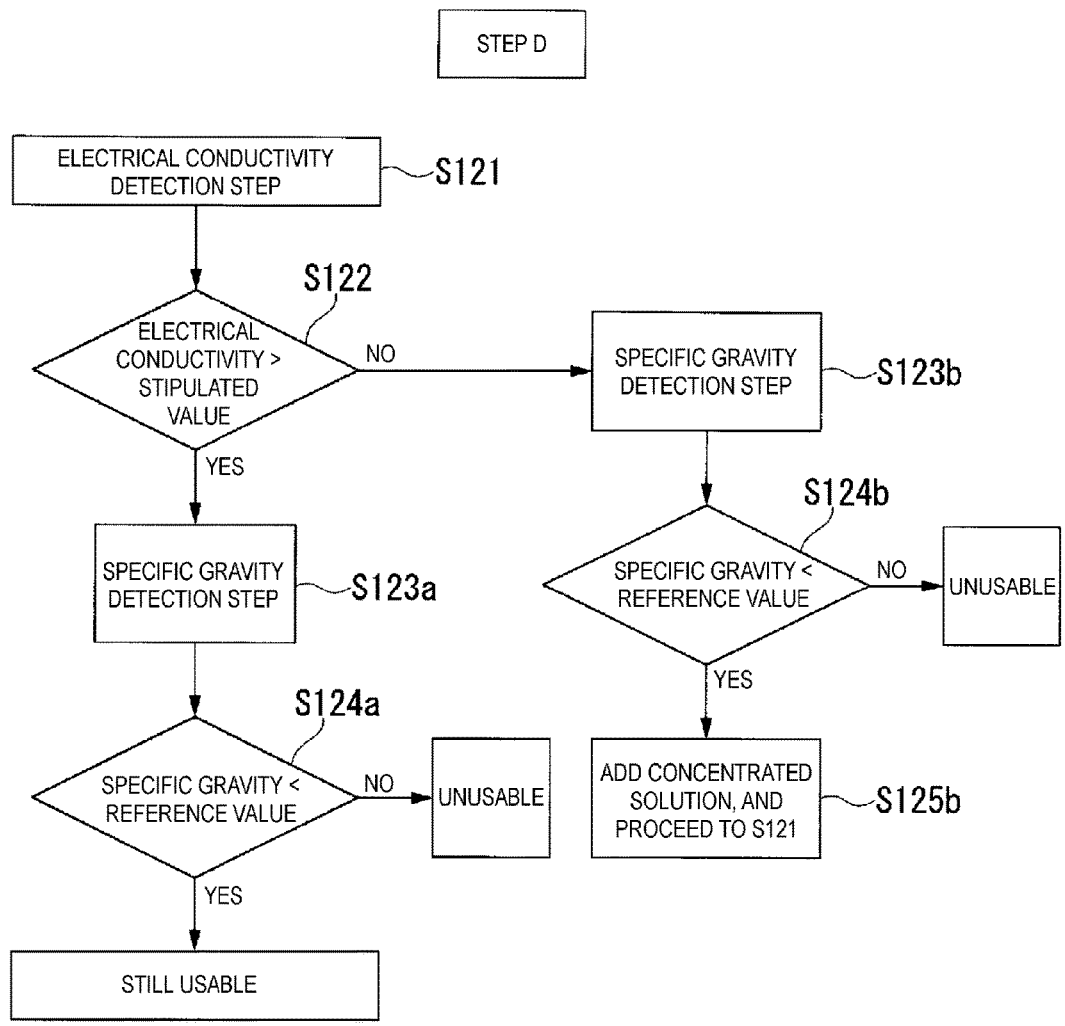
FIG. 7 is a flowchart of step D in FIG. 5.

FIGS. 5 to 7 are flowcharts of the method for determining whether an acidic aqueous solution is usable according to the second embodiment. The method for determining whether an acidic aqueous solution is usable according to the second embodiment comprises, for example, a liquid volume detection step S111, a liquid volume determination step S112, electrical conductivity detection steps S113 and S121, electrical conductivity determination steps S114 and S122, specific gravity detection steps S115a, S115b, S123a, and S123b, and determination steps S116a, S116b, S124a, and S124b.

Details of the method for determining whether an acidic aqueous solution is usable according to the second embodiment will be described below.

First, the liquid volume of the acidic aqueous solution is detected (liquid volume detection step S111).

Then, it is determined whether the liquid volume exceeds a stipulated volume (liquid volume determination step S112). When the liquid volume is equal to or less than the stipulated volume, step C is performed. When the liquid volume exceeds the stipulated volume, step D is performed.
(Step C)

Step C will be described below, using FIG. 6.

In step C, first, the electrical conductivity of the acidic aqueous solution is detected (electrical conductivity detection step S113). Electrical conductivity may be detected by, for example, a platinum black electrode method.

Then, it is determined whether the electrical conductivity exceeds a stipulated value (first threshold) (electrical conductivity determination step S114). When the electrical conductivity exceeds the stipulated value, a specific gravity detection step S115a, in which the specific gravity of the acidic aqueous solution is detected, is performed. When the electrical conductivity is equal to or less than the stipulated value, a specific gravity detection step S115b, in which the specific gravity of the acidic aqueous solution is detected, is performed. Specifically, specific gravity can be measured by the weight method or by a buoy.

In the specific gravity detection step S115a, when the specific gravity is less than a reference value (second threshold), an acidic aqueous solution is added such that the liquid volume of the acidic aqueous solution exceeds a stipulated volume (acidic aqueous solution addition step S117a), and the process returns again to the liquid volume detection step S111. In the specific gravity detection step S115a, when the specific gravity is equal to or greater than the reference value, the acidic aqueous solution is determined to be unusable (determination step S116a). When the acidic aqueous solution is determined to be unusable in this manner, the method for determining whether an acidic aqueous solution is usable according to the present embodiment ends.

In the specific gravity detection step S115b, when the specific gravity is less than the reference value, a concentrated acidic aqueous solution (hydrochloric acid) is added (concentrated-solution addition step S117b), and the process returns again to the electrical conductivity detection step S113. In the specific gravity detection step S115b, when the specific gravity is equal to or greater than the reference value, the acidic aqueous solution is determined to be unusable (determination step S116b).
(Step D)

Step D will be described below, using FIG. 7.

In step D, similar to step C, first, the electrical conductivity is detected (electrical conductivity detection step S121).

Then, it is determined whether the electrical conductivity exceeds a stipulated value (first threshold) (electrical conductivity determination step S122). When the electrical conductivity exceeds the stipulated value, a specific gravity detection step S123a, in which the specific gravity of the acidic aqueous solution is detected, is performed. When the electrical conductivity is equal to or less than the stipulated value, a specific gravity detection step S123b, in which the specific gravity of the acidic aqueous solution is detected, is performed.

In the specific gravity detection step S123a, when the specific gravity is less than a reference value (second threshold), it is determined that an acidic aqueous solution can be further used. In the specific gravity detection step S123a, when the specific gravity is equal to or greater than the reference value, the acidic aqueous solution is determined to be unusable (determination step S124a).

In the specific gravity detection step S123b, when the specific gravity is less than the reference value, a concentrated acidic aqueous solution is added, and the process returns again to the hydrochloric acid concentration detection step S121. In the specific gravity detection step S123b, when the specific gravity is equal to or greater than the reference value, the acidic aqueous solution is determined to be unusable (determination step S124b).

Figure 8:
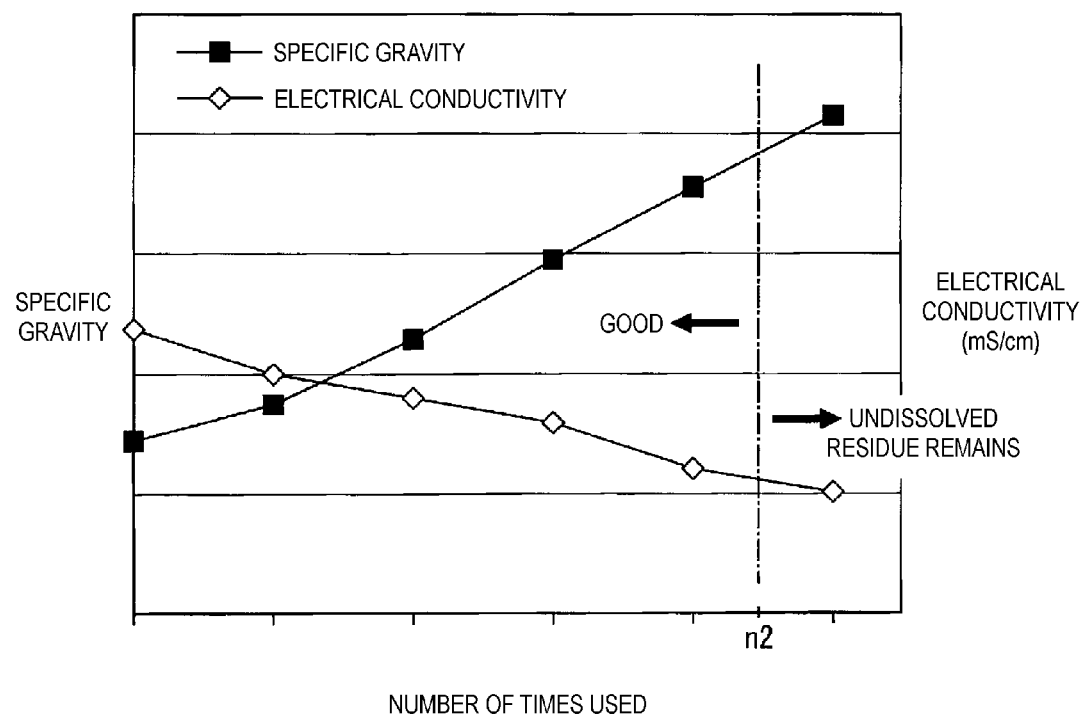
FIG. 8 is a drawing illustrating the relationship between the number of times an acidic aqueous solution is used and specific gravity, and the relationship between the number of times an acidic aqueous solution is used and electrical conductivity.

FIG. 8 illustrates the relationship between the number of times the acidic aqueous solution is used and the electrical conductivity detected in the electrical conductivity detection step S121, and the relationship between the number of times the acidic aqueous solution is used and the specific gravity detected in the specific gravity detection steps S123a and S123b. In FIG. 8, the stipulated value of electrical conductivity and the reference value of specific gravity are indicated by a single dot-dash line. In FIG. 8, it is seen that the an acidic aqueous solution is usable up to n2 times, which is below the stipulated value of electrical conductivity and the reference value of specific gravity.

The stipulated value of electrical conductivity and the reference value of specific gravity can be optionally preset in accordance with the size of the member for gas turbines, the thickness of the coating layer, and the like.

According to the method for determining whether an acidic aqueous solution is usable according to the second embodiment described above, the same advantageous effects as the method for determining whether an acidic aqueous solution is usable according to the first embodiment are exhibited.

In the second embodiment, electrical conductivity and specific gravity are detected. The method for determining whether an acidic aqueous solution is usable can be performed more easily because electrical conductivity and specific gravity can be detected in a shorter time using compact devices.

The method for determining whether an acidic aqueous solution is usable that are embodiments of the present invention has been described above, but the present invention is not limited thereto, and may be modified as appropriate within a range that does not deviate from the technical concept of the invention.

In the above embodiments, the case where Co concentration and hydrochloric acid concentration are detected has been described in the first embodiment and the case where specific gravity and electrical conductivity are detected has been described in the second embodiment, but Co concentration and electrical conductivity, or specific gravity and hydrochloric acid concentration, may also be detected. The same advantageous effects as the above embodiments are exhibited in these cases as well.

In the above embodiments, it was described that the method for determining whether an acidic aqueous solution is usable comprises a liquid volume determination step, but it may not necessarily comprise the liquid volume determination step.

In the above embodiments, the case where Co concentration (concentration of a specific metal) or specific gravity was detected after hydrochloric acid concentration or electrical conductivity was detected, but it is also acceptable if hydrochloric acid concentration or electrical conductivity is detected after Co concentration (concentration of a specific metal) or specific gravity is detected.

INDUSTRIAL APPLICABILITY

According to the above method for determining whether an acidic aqueous solution is usable, it can be determined whether an acidic aqueous solution (strong acid washing solution) that removes a coating layer formed on the surface of a member for gas turbines is usable.

The invention claimed is:

1. A method for determining whether an acidic aqueous solution is usable in pickling treatment that peels a coating layer on a surface of a member for a gas turbine, the method comprising:
   a first detection step of detecting a solution concentration of the acidic aqueous solution after the pickling treatment;
   a second detection step of detecting a concentration of a specific metal in the acidic aqueous solution after the pickling treatment, the metal being contained in the coating layer;
   a concentrated-solution addition step of newly adding a concentrated acidic aqueous solution when the solution concentration is equal to or less than a predetermined first threshold; and
   a determination step of determining that the acidic aqueous solution is unusable when the concentration of the specific metal is equal to or higher than a predetermined second threshold.

2. The method for determining whether an acidic aqueous solution is usable according to claim 1, further comprising a liquid volume determination step of determining whether a liquid volume of the acidic aqueous solution exceeds a stipulated volume, wherein
   in the liquid volume determination step, when the liquid volume is determined to be equal to or less than the stipulated volume, the method comprises:
   a first detection step of detecting a solution concentration of the acidic aqueous solution after the pickling treatment;
   a second detection step of detecting a concentration of a specific metal in the acidic aqueous solution after the pickling treatment, the metal being contained in the coating layer;
   a concentrated-solution addition step of newly adding a concentrated acidic aqueous solution when the solution concentration is equal to or less than a predetermined first threshold;
   an acidic aqueous solution addition step of newly adding an acidic aqueous solution when the solution concentration exceeds the predetermined first threshold; and
   a determination step of determining that the acidic aqueous solution is unusable when the concentration of the specific metal is equal to or higher than a predetermined second threshold.

3. The method for determining whether an acidic aqueous solution is usable according to claim 2, wherein, in the first detection step, electrical conductivity is detected instead of the solution concentration,
   in the concentrated-solution addition step, a concentrated acidic aqueous solution is newly added when the electrical conductivity is equal to or less than a predetermined first threshold, and
   in the acidic aqueous solution addition step, an acidic aqueous solution is newly added when the electrical conductivity exceeds a predetermined first threshold.

4. The method for determining whether an acidic aqueous solution is usable according to claim 1, wherein, in the first detection step, electrical conductivity is detected instead of the solution concentration, and in the concentrated-solution addition step, a concentrated acidic aqueous solution is newly added when the electrical conductivity is equal to or less than a predetermined first threshold.

5. The method for determining whether an acidic aqueous solution is usable according to claim 1, wherein, in the second detection step, specific gravity is detected instead of the concentration of a specific metal, and in the determination step, the acidic aqueous solution is determined to be unusable when the specific gravity is equal to or higher than a predetermined second threshold.

6. The method for determining whether an acidic aqueous solution is usable according to claim 1, wherein the acidic aqueous solution is hydrochloric acid.

* * * * *